United States Patent
Kelly et al.

(10) Patent No.: US 10,363,514 B2
(45) Date of Patent: Jul. 30, 2019

(54) PROTECTING AN OPTICAL PARTICLE SENSOR FROM PARTICULATE DESPOSITS BY THERMOPHORESIS

(71) Applicant: KONINKLIJKE PHILIPS N.V., Eindhoven (NL)

(72) Inventors: Declan Patrick Kelly, Eindhoven (NL); Michael Martin Scheja, Eindhoven (NL); Cornelis Reinder Ronda, Eindhoven (NL); Koray Karakaya, Eindhoven (NL); Jan Frederik Suijver, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 162 days.

(21) Appl. No.: 15/557,492

(22) PCT Filed: Mar. 16, 2016

(86) PCT No.: PCT/EP2016/055615
§ 371 (c)(1),
(2) Date: Sep. 12, 2017

(87) PCT Pub. No.: WO2016/156035
PCT Pub. Date: Oct. 6, 2016

(65) Prior Publication Data
US 2018/0056228 A1    Mar. 1, 2018

(30) Foreign Application Priority Data

Mar. 27, 2015   (WO) ................ PCT/CN2015/075276
May 6, 2015     (EP) .................................... 15166494

(51) Int. Cl.
*B01D 49/02*       (2006.01)
*B01D 51/02*       (2006.01)
(Continued)

(52) U.S. Cl.
CPC ............. *B01D 49/02* (2013.01); *B01D 51/02* (2013.01); *G01N 1/2247* (2013.01); *G01N 15/02* (2013.01);
(Continued)

(58) Field of Classification Search
CPC ........ B01D 51/02; B01D 49/00; B01D 49/02; G01N 1/22; G01N 1/2247
(Continued)

(56) References Cited

U.S. PATENT DOCUMENTS 4,675,031 A * 6/1987 Sinnar .................... B01D 47/05
                                                        261/152
2002/0159215 A1   10/2002  Siess
(Continued)

FOREIGN PATENT DOCUMENTS

CN    103349879 A     10/2013
DE    102008041809 A1   3/2010
(Continued)

OTHER PUBLICATIONS

C. He and G. Ahmadi, "Particle Deposition with Thermophoresis in Laminar and Turbulent Duct Flows", Aerosol Science and Technology 29: 525-546 (1998).
(Continued)

*Primary Examiner* — Robert A Hopkins

(57) ABSTRACT

The invention provides a sensor device which comprises an input flow channel (10) for receiving a gas flow with entrained matter to be sensed. A thermophoretic arrangement (14a, 14b) is used to induce a thermophoretic particle movement from a first, warmer, region (16) of the input flow channel to a second, cooler, region (18) of the input flow channel (10). A sensor (24) comprises a particle sensor component at or downstream of the first region (16) of the input flow channel (10). The invention provides the benefit
(Continued)

Figure 1:
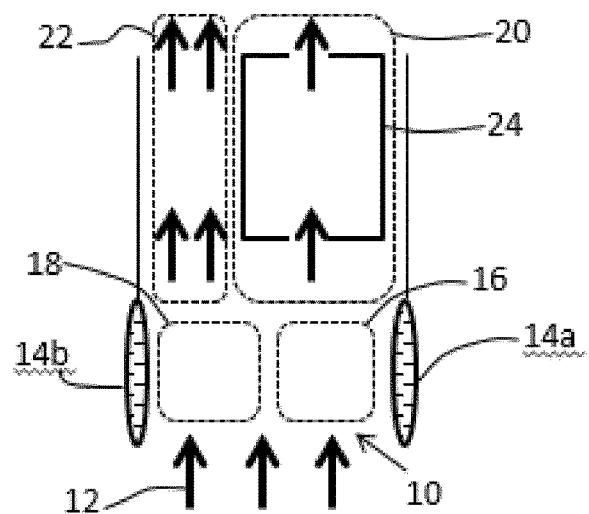
Figure 2:
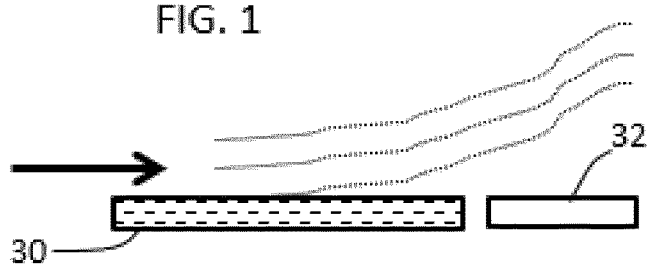

of pre-filtering (e.g. removal of most suspended solids/liquids) without the need for a physical filter that can become blocked.

14 Claims, 4 Drawing Sheets

(51) Int. Cl.
  *G01N 1/22* (2006.01)
  *G01N 21/15* (2006.01)
  *G01N 21/53* (2006.01)
  *G01N 15/06* (2006.01)
  *G01N 15/02* (2006.01)
  *G01N 15/00* (2006.01)

(52) U.S. Cl.
  CPC ............ *G01N 15/06* (2013.01); *G01N 21/15* (2013.01); *G01N 21/53* (2013.01); *G01N 2015/0019* (2013.01); *G01N 2015/0046* (2013.01); *G01N 2015/0693* (2013.01); *G01N 2021/155* (2013.01)

(58) Field of Classification Search
  USPC .................................................. 96/417; 95/1
  See application file for complete search history.

(56) References Cited

U.S. PATENT DOCUMENTS

| | | |
|---|---|---|
| 2006/0066834 A1 | 3/2006 | Phillips |
| 2009/0019918 A1 | 1/2009 | Baars |
| 2011/0114744 A1 | 5/2011 | Ricciardi |
| 2012/0017665 A1 | 1/2012 | Wolst |
| 2013/0235357 A1 | 9/2013 | Delgado |
| 2014/0231659 A1 | 8/2014 | Chilese |

FOREIGN PATENT DOCUMENTS

| | | | | |
|---|---|---|---|---|
| GB | 2319191 A | | 5/1998 | |
| GB | 2339398 A | * | 1/2000 | ............ B01D 45/12 |
| JP | 57131036 A | | 8/1982 | |
| KR | 20130134243 A | | 12/2013 | |
| WO | WO2019053289 A1 | * | 3/2019 | ............... G01N 1/22 |

OTHER PUBLICATIONS

Anita Lloyd Spetz and Robert Bjorklund, "Soot sensors for a healthy environment (SootSens)", Dec. 2009.

\* cited by examiner

PROTECTING AN OPTICAL PARTICLE SENSOR FROM PARTICULATE DESPOSITS BY THERMOPHORESIS This application is the U.S. National Phase application under 35 U.S.C. § 371 of International Application No. PCT/EP2016/055615, filed on Mar. 16, 2016, which claims the benefit of International Application No. PCT/CN2015/075276 filed on Mar. 27, 2015 and International Application No. 15166494.3 filed on May 6, 2015. These applications are hereby incorporated by reference herein.

FIELD OF THE INVENTION

This invention relates to a sensor device and method for detecting targets within a gas flow, such as particulate matter.

BACKGROUND OF THE INVENTION

DE102008041809 discloses a method for operating a particle sensor. In a phase in which no measurements take place, a heater is set to a temperature to avoid particle deposition at electrodes used for particle measurement. Avoiding particle deposition can, for example, be based on thermophoresis.

Airborne particle pollution, especially particle matter size less than 2.5 μm diameter range (named "PM2.5"), is a big concern for countries like China, where the speed of industrialization stretches the boundaries of regulatory requirements.

As a consequence of increasing consumer empowerment, the demand for information about the air quality of living spaces is increasing. Especially in China, excessive PM2.5 pollution has become a common problem in the last decade. This problem is also validated by continuous measurements in various Chinese cities. The data is publicly available and can be simultaneously monitored by mobile phone applications or through the web.

Availability of this data as well as continuous national and international media attention has created strong consumer awareness about the problem.

Official outdoor air quality standards define particle matter concentration as mass concentration per unit volume (e.g. $\mu g/m^3$). The average PM2.5 pollution concentration in mainland China has been calculated based on satellite data, and it has been found that the majority of the country exceeds the World Health Organization limits of 10 μg/m3, with some regions reaching and even exceeding PM2.5 concentrations of 100 μg/m3.

Standard reference measurement methods are based on measuring the mass of deposited or captured particles per air sampling volume for example using a quartz crystal microbalance, a tapered resonator, an impactor, or weighing filters and sieves. There is also a desire to detect specific chemicals within the air, in addition to (or instead of) measuring particle concentrations.

For many sensors, the operation principles result in a response to other compounds than the target compound, leading to incorrect readings when a target compound and an interfering compound are present simultaneously.

Taking an electrochemical formaldehyde sensor as example, compounds like alcohols and detergents can greatly influence the output, and these other compounds are commonly seen in real home conditions.

A known solution is to put a physical filter in front of the sensor to block suspended solids and liquids, however, over time this filter will get blocked and reduce the air flow through the sensor.

SUMMARY OF THE INVENTION

It is an object of this invention to provide the benefit of pre-filtering (e.g. removal of most suspended solids/liquids) without the need for a physical filter that can become blocked. This pre-filtering function may also be used to selectively protect key components of the sensors.

The invention is defined by the independent claims. The dependent claims define advantageous embodiments.

According to examples in accordance with an aspect of the invention, there is provided a sensor device comprising:
an input flow channel for receiving a gas flow with entrained matter to be sensed;
a heating arrangement to induce thermophoretic particle movement from a first, warmer, region of the input flow channel to a second, cooler, region of the input flow channel;
a sensor comprising a particle sensor component in, or downstream of, the first region of the input flow channel.

This arrangement uses thermophoretic induced movement of entrained matter, in particular particles, to steer matter away from a particle sensor component. In this way it can be controlled which particles are sensed by the particle sensor component.

The heating arrangement may comprise a Peltier heater. This provides an efficient and low cost implementation. The heating arrangement may comprise a thermal coupling between an existing heat-generating component of the system which is provided to perform a non-heating function. For example, a light source generates heat in addition to its main function of generating light. This heat can be coupled to the component to be protected to drive particulate matter away. Alternatively, an active heat source may be provided on or adjacent the component. This may for example be a Joule heating wire grid.

The device may further comprise a cooling arrangement which combines with the heating arrangement to induce the thermophoretic particle movement. This enables more active thermophoretic behavior. The cooling arrangement may also comprise a Peltier device, functioning as a cooler.

The sensor may comprise an optical sensor, and the sensor component comprises a lens or lens cover. The sensor does not need to be in direct contact with the entrained matter since the optical detection can be remote. The heating arrangement may for example be integrated with the lens.

If a sensor component of the optical sensor comprises a lens cover, the lens cover may be optically transparent and electrically conductive. For example, the lens cover may be fabricated from a material that is optically transparent and electrically conductive. The device or the optical sensor may further comprise a means for applying a voltage to the lens cover such that the lens cover heats up during operation. For example, a voltage supply unit adapted for delivering a applying a suitable voltage.

In one arrangement, the first region of the input flow channel couples to a first output flow region and the second region of the input flow channel couples to a second output flow region. The sensor component may then be located in the first output flow region.

Note that the term "couples", for example in the expression "A couples to B", is used to mean that the B is positioned downstream of A when following the prevailing general flow direction. Thus, it does not imply any particular physical channels, but may be achieved only with suitable relative positioning of components.

Thus, in accordance with the invention, the sensor component is either within the warmer part of the input flow channel, or else further downstream, at a corresponding warmer part of the output flow region.

The entrained matter is moved from the relatively warmer region to the relatively cooler region by the thermophoresis, and the sensor component is thus located at a region which has a lower concentration of the entrained matter.

If the input flow channel is large, the thermophoretic effect may be reduced. The input flow channel may then be divided into input sub-channels, each sub-channel having a respective heating arrangement thereby to generate respective first (warmer) and second (cooler) regions of the input sub-channel. The sub-channel first regions may then together couple to the first output flow region and the sub-channel second regions may then together couple to the second output flow region.

This enables the entrained matter to be moved more effectively between the output flow regions.

According to an embodiment of the invention, a space is provided in between the first region and the sensor. The space is provided between the first region of the input flow channel, after the thermophoretic arrangement, and the first output flow region at which the sensor or sensor component is located. This space enables diffusion to take place before sensing. This diffusion is dependent on particle size, so particle filtering takes place before sensing.

According to an embodiment of the invention, a means for changing a length of the space between the first region of the input flow channel and the sensor is present.

According to a particular embodiment of the invention, the thermophoretic arrangement comprises a segmented heating arrangement for inducing the thermophoretic particle movement. The means for changing a length of the space is configured to activate one or more segments of the segmented heating arrangement thereby changing the length of the space. For example, by applying a voltage to one or more segments, the length of the space between the first region of the input flow channel and the sensor changes depending on how many segments are supplied with a voltage. For example, the means for changing a length of the space may comprise de-multiplexing logic to activate appropriate segments. The de-multiplexing logic may be driven by a processor that can be programmed by the user.

According to another particular embodiment of the invention, the sensor and the thermophoretic arrangement are moveable relative to each other. The means for changing a length of the space allows increasing or decreasing the space by moving the thermophoretic arrangement and the sensor relative to each other. For example, a mechanical structure may be provided which features the sensor and the thermophoretic arrangement and which allows the distance between the two elements to be changed.

The device may for example be used for sensing a target in air, and the sensor may for example include a volatile organic compound (VOC) sensor in addition to a particle sensor. Thus the "entrained matter" may be gaseous or particulate.

According to examples in accordance with another aspect of the invention, there is provided a sensing method, comprising:

receiving a gas flow with entrained matter to be sensed at an input flow channel;

prefiltering the gas flow by inducing a thermophoretic particle movement from a first, warmer, region of the input flow channel to a second, cooler, region of the input flow channel; and performing sensing using a sensor which comprises a particle sensor component in, or downstream of, the first region of the input flow channel.

The sensing may be based on the matter present in or downstream of the first region. Alternatively, the sensing may be based on matter present in or downstream of the second region, but there is nevertheless a sensor component in or downstream of the first region.

The method may comprise cooling the gas flow in the input flow channel at a different location to the heating, wherein the heating and cooling combine to induce the thermophoretic particle movement.

The method may be used for sensing VOCs in addition to a particulate matter in air.

These and other aspects of the invention will be apparent from and elucidated with reference to the embodiments described hereinafter.

BRIEF DESCRIPTION OF THE DRAWINGS

Examples of the invention will now be described in detail with reference to the accompanying drawings, in which:

FIG. 1 shows an example of a gas sensor;

FIG. 2 shows how the thermophoretic effect may be used to lift a particulate flow away from a sensor surface;

FIG. 3 shows an optical gas sensor;

FIG. 4 shows how a flow can be divided into sub-channels;

FIG. 5 shows how the thermophoretic effect may be used for a particle filtering approach;

FIG. 6 shows results of modeling the electrophoretic force acting on particles of different sizes; and FIG. 7 shows how the prefiltering can be tuned.

DETAILED DESCRIPTION OF THE EMBODIMENTS

The invention provides a system comprising a particle sensing component, and a heating arrangement to induce thermophoretic particle movement away from the component. This mechanism may be used in a sensor device which comprises an input flow channel for receiving a gas flow with entrained matter to be sensed. The heating arrangement is used to induce thermophoretic particle movement from a first, warmer, region of the input flow channel to a second, cooler, region of the input flow channel. A sensor comprises the particle sensor component) at or downstream of the first region of the input flow channel. This way, filtering can be performed without the need for a physical filter.

In this sensor device, thermophoresis is used to move particles from the air path of sensors or key components of such sensors. In doing so, the sensor or specific components thereof can be protected without the need for a physical filter to block particles.

The force which is induced during thermophoresis depends on the temperature gradient in the gas around the particles and also the temperature gradient within the particles themselves (which depends on the thermal conductivity of the particle). Generally, thermophoresis is a force that affects particles in air and is proportional to the thermal gradient in the air. The gas molecules on the hot side exert a force on the particles, pushing them to the cold side.

To generate the thermophoretic force, a heater can be used. Particles entrained within a gas flow will then be pushed away from the heated surface. To increase the temperature gradient, a cooling element and/or a cold surface with a large thermal mass (e.g. a heat sink) may be placed opposite. Both heating and cooling can be implemented using thermally active components (e.g. Peltier elements).

An alternative is to use an existing hot component of the sensor system. For example a pre-concentrator may generate heat which may be used, and the column section of a micro gas chromatography unit also generates usable heat. The hot components can also be used for facilitating a continuous convection air stream to the sensor compartment.

Examples of the invention applied to sensor devices will first be described.

FIG. 1 shows a schematic illustration of the approach of the invention for a sensor.

It shows a sensor device comprising an input flow channel 10 for receiving a gas flow 12 with entrained matter to be sensed. The gas flow is for example an air flow.

A thermophoretic arrangement is used to induce thermophoretic particle movement from a first, warmer, region 16 of the input flow channel to a second, cooler, region 18 of the input flow channel 10. In the example shown, the thermophoretic arrangement comprises a heater 14a and a cooler 14b on opposite sides of the input flow channel 10.

In this example, the first region 16 of the input flow channel couples to a first output flow region 20 and the second region of the input flow channel couples to a second output flow region 22.

A sensor 24 has a particle sensor component in the first output flow region 20, namely downstream of the first region 16 of the input flow channel. FIG. 1 shows the whole sensor in the first output flow region 20, but parts of the sensor may be remote as will be clear from examples below.

The particles in the gas flow are pushed away from the heating element and thus away from the sensor input. In practice, the thermophoretic force acts only on a limited distance that depends on the thermal gradient.

The distance between heater-cooler and the sensor entrance will be known for a particular implementation and impacts the gas density, which will change due to the temperature change. This can and needs to be corrected for in the processing of the sensor signals, as a changed density will lead to the indication of different sensor values.

For sensors with larger air flow entrances, the air flow to the sensor entrance can be divided into a number of small sub-channels of the appropriate dimensions. Within each sub-channel the air flow can then be divided into two parts: one with particles that exit through a channel outside the sensor entrance and one with particles removed that enters the sensor. Within the sub-channels, thermophoresis can be used to push the particles to the exhaust channel. An example is given below.

The inflow of particles into the device housing (or into sub-compartments within a device) can be controlled by placing a heated grid at the air inlet. The mesh size of the grid may for example be of the order of 0.5 mm. Thermophoresis at the heated grid will then block a proportion of the particles from entering the housing or compartment, while allowing gas molecules to pass. This may for example be desired for gas sensors, where it is desired to prevent particles from entering the gas sensor at all.

In other cases, such grids might be used to control the portion of particles entering the sensor. For example, decreasing the temperature of the grid will allow a larger portion of particles to enter. Increasing the mesh size will have a similar result.

By reducing the portion of particles entering the housing, the accuracy of certain particle sensors can be maintained through a wider range of particle concentrations, provided that changes in the resulting gas densities are known accurately.

In an alternative approach, the heating element can be positioned close to the sensing element of the sensor and used to push the particles away to avoid direct contact with the sensing surface. There is no need to push the particles far from the surface, just enough to avoid direct contact.

FIG. 2 shows a heater 30 having a heating surface which lies in the same plane as the sensing surface of a sensor 32. The sensor is downstream of the heater. The effect of the heating is to lift the gas flow away from the sensor surface, to reduce contamination of the sensor surface.

FIG. 3 shows an example in which there is a gas flow 40 from an inlet 41 to an outlet 42 of the overall sensor device. An infrared LED 44 is used to illuminate the gas flow to enable optical detection of entrained particles based on optical measurements of scattering or reflection.

The optical sensor 46 comprises a photodiode sensor 48 and a focusing lens 50. By placing a heating element before the lens 50 (in the direction of air flow) or by directly heating the lens, the particles can be prevented from directly touching the lens.

For example, the lens may be formed as a transparent material with high thermal conductivity such as sapphire and it may then be in direct contact with a heating element (e.g. a resistive heating element).

So-called garnet lenses or lenses produced of other inorganic materials with cubic crystal structure may be used (these being minerals classes that can also be man-made). Such materials are used in view of their large refractive index, and they may also possess high thermal conductivity. These lenses can be made using a ceramic process, and it is possible to incorporate thin heating wires within such lens designs.

According to an embodiment of the invention, the lens 50 of the optical sensor 46 is covered by a lens cover. The lens cover may be optically transparent and electrically conductive. By heating the lens cover, e.g. by applying a voltage to it, the temperature of the lens increases thereby reducing or preventing particle precipitation on the lens. According to a particular embodiment, the lens cover is fabricated from an optical transparent material that is electrically conductive. For example, the lens cover may comprise fine conductive particles that do not disturb optical signals propagating through the lens cover. The material of the lens cover may comprise InO2, (In,Sn)O2; ZnO:Ga or ZnO:Ga, graphene or other materials like PEDOT. According to an embodiment of the invention, the material of the lens cover is adapted to absorb less than 50% of light originating from illuminated particles of interest. Preferably, the material of the lens cover is adapted to absorb less than 30% of light originating from illuminated particles of interest. More preferably, the material of the lens cover is adapted to absorb less than 20% of light originating from illuminated particles of interest.

In this way, the input flow channel 40 has a first, warmer, region 53 and a second, cooler, region 54. The sensor component in this example is the lens 50 which is located in the warmer region 53 of the input flow channel, rather than further downstream. Preferably, the heating has an effect at least a short distance before the input flow channel reaches the sensor component, so that the thermophoretic effect can function. Thus, even in this case, the sensor component is downstream of the part of the input flow channel at which heating is first effective, even if the heater is integrated into the sensor component itself. In particular, there will be a thermal gradient away from the heater which will be met by the incoming entrained matter before it reaches the component itself.

Figure 3:
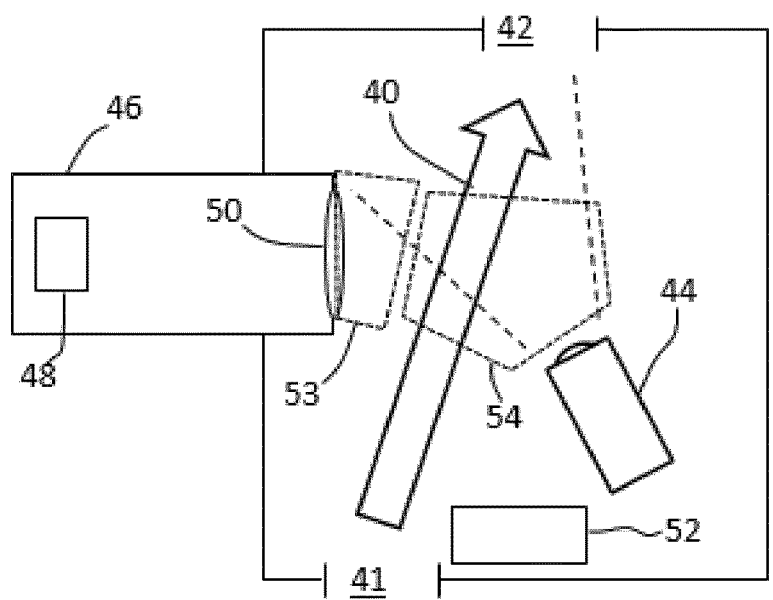
Figure 4:
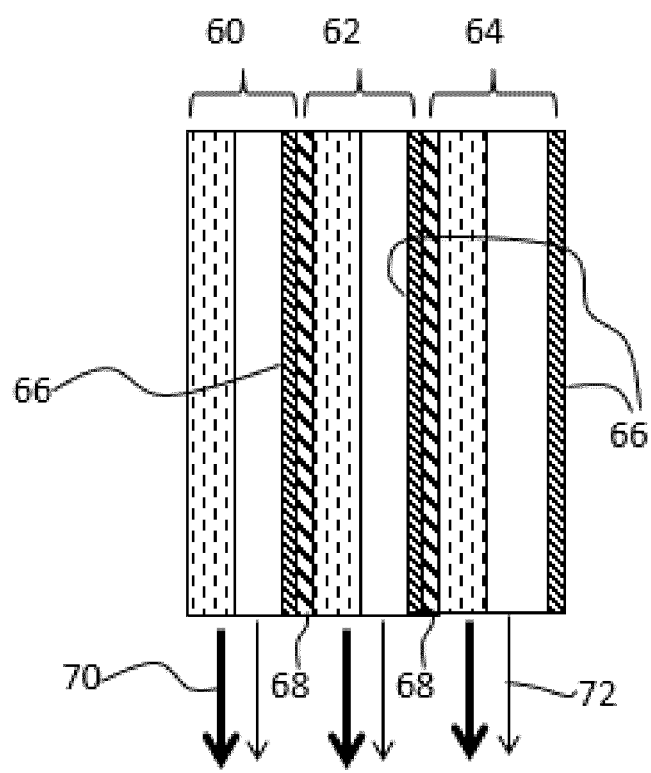

FIG. 3 also shows a separate heater 52 for inducing convective flow through the sensor device.

In general, many methods can be used to heat the lens. A resistive heater may be used to directly heat the lens material or a lens cover as mentioned above, but alternatives include near infra-red heating and ultrasonic heating. The heating method of course should not interfere with the operation of the sensor.

One example of a heating element is a Peltier heating element. Peltier elements can be electrically switched between heating and cooling, for example allowing the direction of particle movement to be reversed. They also enable simple implementation of heating and cooling on opposite sides of the input flow channel.

Controlled switching between heating and cooling enables dynamic operation of the system, giving additional accuracy by mass estimation of the particles. This is discussed further below. Similar arguments hold for controlled heating steps.

The thermophoresis force is proportional to the temperature gradient and the inverse of the mean air temperature. For a given configuration, the heat supplied must be sufficient to generate the force necessary to move the particles. Increased air temperature requires a larger temperature gradient to achieve the same effect, therefore the heat applied may be varied based on the ambient temperature. Alternatively, a fixed heating level may be selected to ensure the desired result within an expected or operating temperature range. The heating level will for example depend on the area and length of the heating element, which thus depend on the expected particle density and required distance to displace the particles.

As explained above, if the sensor entrance is too large, the thermophoretic force (with a realistic temperature gradient) may not be able to displace the particles sufficiently far to remove them from the path of the sensor component to be protected.

FIG. 4 shows a grid of three separate sub-channels 60, 62, 64. Each sub-channel comprises its own heater 66, and there is thermal insulation 68 between the channels. In this way, the input flow channel is divided into input sub-channels, each sub-channel having a respective heating arrangement thereby to generate respective first and second regions of the input sub-channel.

FIG. 4 shows a cross section in plain view, i.e. and the lengths of the sub-channels shown are in the general direction of the overall air flow. An end view, i.e. the front face as seen by the air flow, may then comprise a two dimensional or three dimensional array of grid openings, each one corresponding to one of the sub-channels.

In FIG. 4, each input sub-channel causes a flow (shown by bold arrows 70) where there is a relatively high concentration of particles and a flow (shown by faint arrows 72) where there is a relatively low concentration of particles. The flow 70 will lead to an exhaust port, completely bypassing the sensor in the case of a gas sensor, or else it will lead to the particle detection area in the case of a particle sensor, but away from components of the sensor which are to be protected from contamination. These components are in the path of the flow 72.

The sub-channel first regions together couple to the first output flow region and the sub-channel second regions together couple to the second output flow region. The required channel coupling arrangement is not shown in FIG. 4.

Particles will move from the heated side to concentrate the particles in the exhaust streams. Sufficient insulating material 68 is used to separate the channels to avoid both sides of the surrounded channels (i.e. the middle channel and right in this example) becoming heated. If the sensor is used continuously, then over time the internal components will nevertheless reach thermal equilibrium. This can be prevented by using a pulsed or sequential operation, which is practical for a consumer solution, or by active cooling of the cold surface.

A variation is to use a single narrow channel that is wide at the separation region of the input flow channel but narrow (or funnel like) at the entrance to the sensor.

FIG. 5 shows how the arrangement may be used to enable particle size selection.

In the arrangement of FIG. 5, a space 80 is provided between the first region 16 of the input flow channel 10, after the heating/cooling arrangement 14*a*, 14*b*, and the first output flow region 20 where the sensor 24 is located. This space is used in this example to allow diffusion of particles.

As shown in FIG. 5(*a*), all particles are first concentrated at one side of the input flow region 10 by thermophoresis driven by the heating arrangement 14*a*, 14*b*. All particles are accelerated to a certain forward velocity by the air flow.

Once they leave the input flow region 10 and enter the space 80, the thermophoretic force is no longer acting, but they keep their velocity in the forward (y axis) direction due to the air flow. The concentration gradient then forces the particles in the transverse (x axis).

This diffusion is dependent on the particle size.

In particular, the particle diffusion is dependent on the size and shape of the aerosol particles, resulting in slower diffusion of larger particles than smaller ones:

$$D = \frac{k \cdot T \cdot C_c}{3 \cdot \pi \cdot \eta \cdot d_p} \ [\mathrm{m^2/s}]$$

Herein,

D is the particle diffusion coefficient
k is the Boltzman constant
T is the temperature
$C_c$ is the Cunningham slip correction factor
$\eta$ is the gas viscosity
$d_p$ is the particle diameter.

As a result, smaller particles will experience a stronger deviation in the x-axis direction compared to larger ones. FIG. 5(*a*) shows the movement of larger particles in the inlaid graph, and FIG. 5(*b*) shows the movement of smaller particles in the inlaid graph.

The space 80 can in this way be used as a low-pass filter, since it only allows particles below a certain size to enter the sensor.

The threshold of this filter can be tuned, for example by changing the length of the space 80 or by controlling the air velocity.

FIG. 5(*c*) shows the resulting particle distribution and shows how the larger particles are diverted away from the sensor.

The ability for thermophoresis to create the desired particle movement has been assessed using modeling. For this purpose, clay particles are modeled in air through a 10 mm wide and 0.5 mm high channel (in cross section) and with 10 mm length. A gas flow of 10 ml/minute is used.

The thermophoretic effect is modeled with heating temperatures of 40 degrees, 60 degrees and 100 degrees on the heated side and 21 degrees at the opposite side.

Figure 6:
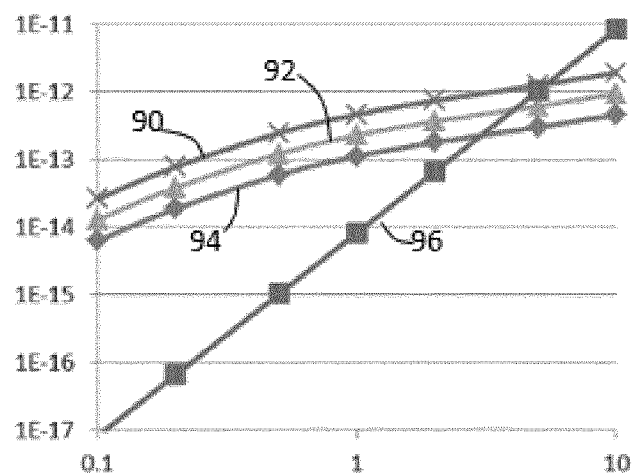
Figure 7:
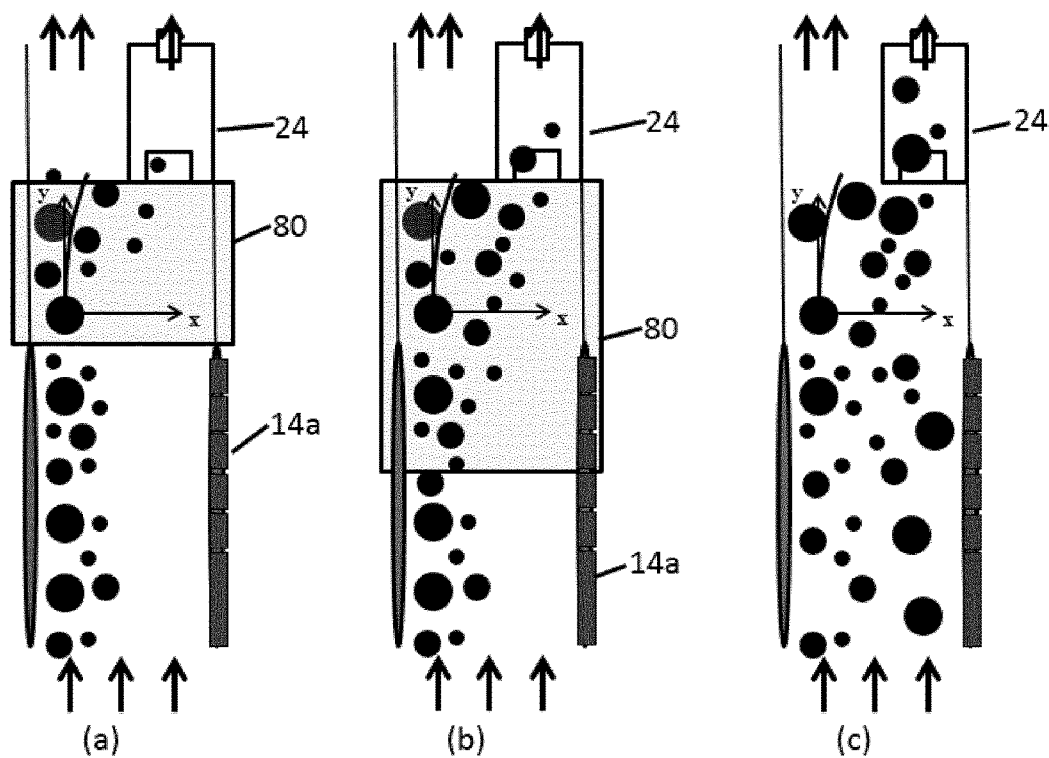

FIG. 6 shows the results, as a plot of the force acting on the particles (y-axis) as a function of the particle size (x-axis). Plot 90 is for the 100 degree heating, plot 92 is for the 60 degree heating and plot 94 is for the 40 degree heating. Plot 96 shows the gravity force.

It can be seen that at a certain particle size, the gravity force becomes dominant. The larger the temperature gradient, the larger the particle sizes that can be moved using the thermophoretic effect. In this simulation, the gravity force overtakes the thermophoretic force at particle sizes of 3.0, 4.0 and 5.4 µm for the three temperature gradients.

Figure 5:
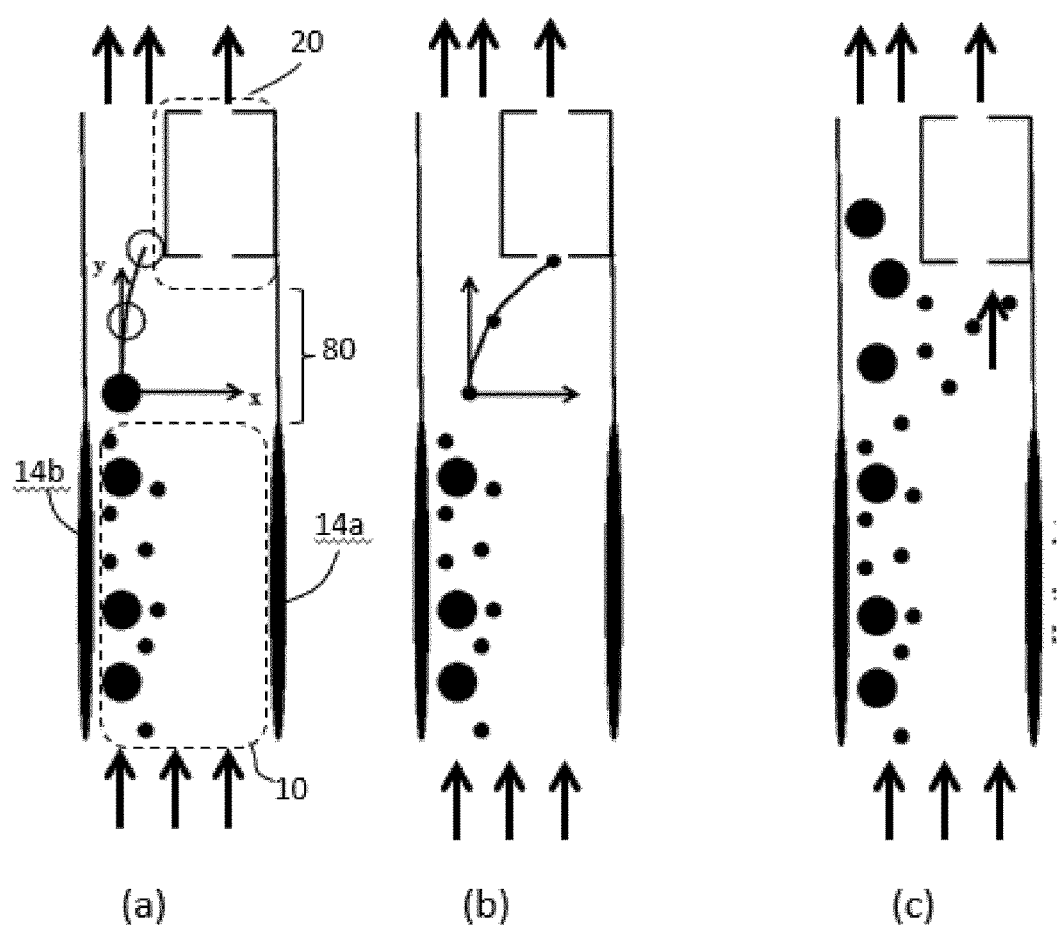

FIGS. 5 and 6 show how the level of heating (or more particularly the thermal gradient) influences the way particles of different size (or mass) behave. The level of heating can thus be used as a control parameter. By progressively increasing the size range of particles drawn away from the particle sensor, a series of sensor measurements can be processed to derive particle concentration information as a function of particle size.

This particle size (or mass) dependent movement may be controlled by controlling a heating element, or by controlling cooperating heating and cooling elements. If a heating element is switchable between heating and cooling, as is the case for a Peltier heating element, the particle direction may be reversed. For example all particles may be progressively drawn from one side to the other, and in a different sequence they may all be progressively drawn from the other side to the one side. This provides further sensor information which may be used to increase the accuracy of particle sensing as a function of particle size.

FIG. 7 is a variation of FIG. 5 and illustrates an embodiment where the thermophoretic arrangement 14*a*, 14*b* combined with the space 80 forms a prefilter for the sensor 24. The prefilter can be tuned by varying the length of the space 80 by partially switching on or off segments of the heater 14*a*. In FIG. 7(*a*), the entire heater 14*a* is switched on, and only small particles reach the sensor 24. In FIG. 7(*b*), only a lower part of the heater 14*a* is switched on, and as a result the space 80 becomes larger and also medium size particles reach the sensor 24. In FIG. 7(*c*), no segment of the heater 14*a* is switched on, as a result the space 80 becomes even larger and also large particles reach the sensor 24. In an alternative prefilter tuning example, the entire heater 14*a* may be placed at a larger distance from the sensor 24 by moving the sensor 24 and/or the heater 14*a*, thereby increasing the length of the space 80. The pre-filter gives a user control over which particle sizes can reach the sensor. It is an advantage of the invention that the pre-filter does not get blocked. This extends the life-time of the particle filter.

The detailed examples above all relate to sensor applications.

The heater 30 may be implemented by any intentional design features which increase the surface temperature. For example, the optical component may be at the surface of the packaging of a system. If the system includes a component which gives out a significant amount of heat (such as light source or a high power semiconductor component), the device packaging may be designed to provide thermal coupling between the heat-generating component and the package surface. This also helps with thermal stabilization of the heat generating component (e.g. the light source) and also provides a heated surface for performing a thermophoresis function. The heat-generating component then has a main function (e.g. giving out light) which is a non-heating function.

Alternatively, an active heat source may be used for example a wire grid for Joule heating. A Peltier heating element is also possible, although this may increase the complexity more than is desired. The approach may for example be used in a TO-5 package to heat an optical output window forming a cap at the package surface. In electronics, TO-5 is a designation for a standardized metal semiconductor package used for transistors and some integrated circuits. TO stands for "transistor outline" and refers to a series of technical drawings produced by JEDEC. Building a thermal link between the back end of the active component (inside the package) and the cap will help keep the optical window clean. In a similar fashion, active heating may be used.

The invention can be applied to air purifiers with sensors or to standalone air sensors.

In examples of the invention, the heating is to drive particles away from a component, and that component is thus on the heated side. However, this may be only one mode of operation of the device. As explained above, the heating direction may be alternated. In this case, the device may have one mode where the component is on the hot side and one mode where the component in on the cold side. Thus, there may be a mode of operation in which the component is protected, and another mode of operation for a particular sensing function or sensing sequence.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

Any reference signs in the claims should not be construed as limiting the scope.

The invention claimed is:

1. A particle sensor comprising:

an input flow channel for receiving a gas flow with entrained matter to be sensed;

a thermophoretic arrangement to induce a thermophoretic particle movement from a first region of the input flow channel to a second region of the input flow channel, the first region being warmer than the second region; and a sensor comprising a particle sensor component which is located in, or downstream of the first region of the input flow channel;

wherein the first region of the input flow channel couples to a first output flow region and the second region of the input flow channel couples to a second output flow region.

2. A particle sensor as claimed in claim 1, wherein the thermophoretic arrangement comprises a Peltier heater.

3. A particle sensor as claimed in claim 1, wherein the thermophoretic arrangement comprises a cooling arrangement which combines with a heating arrangement to induce the thermophoretic particle movement, wherein the cooling arrangement comprises a Peltier cooler.

4. A particle sensor as claimed in claim 1, wherein the sensor comprises an optical sensor, wherein a sensor component of the optical sensor comprises a lens or lens cover and wherein the thermophoretic arrangement is integrated with the lens or lens cover.

5. A particle sensor as claimed in claim 1, wherein the sensor comprises an optical sensor, wherein a sensor component of the optical sensor comprises a lens, wherein the lens is covered by a lens cover, and wherein the lens cover is optically transparent and electrically conductive.

6. A particle sensor as claimed in claim 1, wherein the input flow channel is divided into input sub-channels, each sub-channel having a respective heating arrangement thereby to generate respective first and second regions of the input sub-channel, wherein the sub-channel first regions together couple to the first output flow region and the sub-channel second regions together couple to the second output flow region.

7. A particle sensor device as claimed in claim 6, wherein a space is provided between the first region of the input flow channel, after the heating arrangement, and the first output flow region.

8. A particle sensor as claimed in claim 7, comprising a means for changing a length of the space.

9. A particle sensor according to claim 8, wherein the thermophoretic arrangement comprises a segmented heating arrangement, and wherein the means for changing a length of the space is configured for activating one or more segments of the segmented heating arrangement thereby changing the length of the space.

10. A particle sensor according to claim 8, wherein the sensor and the thermophoretic arrangement are moveable relative to each other, and wherein the means for changing a length of the space allows changing the length of the space by moving the thermophoretic arrangement and the sensor relative to each other.

11. A particle sensor as claimed in claim 1, for sensing a volatile organic compound in addition to sensing particles.

12. A particle sensing method comprising:
receiving a gas flow with entrained matter to be sensed at an input flow channel;
prefiltering the gas flow by inducing a thermophoretic particle movement from a first region of the input flow channel to a second region of the input flow channel, the first region being warmer than the second region, and wherein the first region of input flow channel couples to a first output flow region and the second region of the input flow channel couples to a second output flow region; and
performing sensing using a particle sensor component located in, or downstream of the first region of the input flow channel.

13. A method as claimed in claim 12, further comprising cooling the gas flow in the input flow channel at a different location to heating the gas flow in the input flow channel wherein the heating and cooling combine to induce the thermophoretic particle movement.

14. A method as claimed in claim 12, comprising heating separately within sub-channels of the input flow channel thereby to generate respective first and second regions with each sub-channel, and coupling together the sub-channel first regions to a first output flow region and coupling together the sub-channel second regions to a second output flow region.

* * * * *